(12) United States Patent
Mustafa (10) Patent No.: US 6,387,913 B1
(45) Date of Patent: May 14, 2002

(54) METHOD OF TREATING AIRWAY DISEASES WITH COMBINED ADMINISTRATION OF $A_{2B}$ AND $A_3$ ADENOSINE RECEPTOR ANTAGONISTS

(76) Inventor: S. Jamal Mustafa, 419 Kempton Dr., Greenville, NC (US) 27834

( * ) Notice: Subject to any disclaimer, the term of this patent is extended or adjusted under 35 U.S.C. 154(b) by 0 days.

(21) Appl. No.: 09/997,948

(22) Filed: Nov. 30, 2001

Related U.S. Application Data (60) Provisional application No. 60/251,962, filed on Dec. 7, 2000.

(51) Int. Cl.$^7$ .................. A61K 31/505; A61K 31/52
(52) U.S. Cl. ........................... 514/260; 514/264
(58) Field of Search ................... 514/260, 264

(56) References Cited

U.S. PATENT DOCUMENTS 6,117,878 A * 9/2000 Linden .................. 514/263

* cited by examiner

Primary Examiner—Raymond Henley, III
(74) Attorney, Agent, or Firm—Jenkins & Wilson, P.A.

(57) ABSTRACT

Methods and compositions for treating airway diseases such as asthma and inflammation are described. The methods utilize the concurrent administration of an $A_3$ adenosine receptor antagonist and an $A_{2B}$ adenosine receptor antagonist (either separately or put together chemically in a single molecule having both $A_3$ and $A_{2B}$ blocking effect), for both receptor binding agents and antisense oligonucleotides. The compositions contain both an $A_3$ adenosine receptor antagonist and an $A_{2B}$ adenosine receptor antagonist, together in a pharmaceutically acceptable carrier.

6 Claims, 7 Drawing Sheets

METHOD OF TREATING AIRWAY DISEASES WITH COMBINED ADMINISTRATION OF $A_{2B}$ AND $A_3$ ADENOSINE RECEPTOR ANTAGONISTS

CROSS REFERENCE TO RELATED APPLICATIONS

This application is based on and claims priority to U.S. Provisional Application Ser. No. 60/251,962, filed Dec. 7, 2000, herein incorporated by reference in its entirety.

GRANT STATEMENT

This work was supported by grant HL50049 from the National Institutions of Health (NIH). Thus, the United States Government has certain rights in the invention.

FIELD OF THE INVENTION

The present invention concerns methods and compositions useful for the treatment of airway diseases such as asthma.

BACKGROUND OF THE INVENTION

Asthma is one of the most common diseases in industrialized countries, and in the United states accounts for about 1% of all health care costs (K. Weiss et al., *New Eng. J. Med.* 326, 862–866 (1992)). An alarming increase in both the prevalence and mortality of asthma over the past decade has been reported (Asthma-United States, 1980–1990, MMWR 41, 733–735 (1992)), and occupational asthma is predicted to be the preeminent occupational lung disease in the near future (M. Chan-Yeung and J. Malo European Resp. J. 7, 346–371 (1994)).

PCT Application WO96/40266 to Nyce (Dec. 19, 1996) describes a method of reducing bronchoconstriction in a subject such as an asthma patient by administering an $A_1$ or $A_3$ adenosine receptor antisense oligonucleotide.

PCT Application WO96/40162 to Nyce (Dec. 19, 1996) (see also U.S. Pat. No. 5,994,315) describes a method of treating airway disease in a subject by administering an antisense oligonucleotide, particularly certain adenosine receptor antisense oligonucleotides.

U.S. Pat. No. 5,932,557 to Mustafa et al. concerns adenosine $A_1$ antisense oligonucleotides in the treatment of alcohol and marijuana-induced psychomotor impairments.

There remains a need for new methods and compositions for the treatment of asthma, as well as other airway diseases.

SUMMARY OF THE INVENTION

A first aspect of the invention is a method of treating an airway disease (including inflammation with and without asthma) such as asthma in a subject in need of such treatment, comprising concurrently administering to the subject an $A_3$ adenosine receptor antagonist and an $A_{2B}$ adenosine receptor antagonist (either separately or in a single molecule or composition having both receptor blocking activities), in an amount effective to treat said disease.

A second aspect of the present invention is a composition useful for treating an airway disease in a subject in need of such treatment, comprising, in a pharmaceutically acceptable carrier, an $A_3$ adenosine receptor antagonist and an $A_{2B}$ adenosine receptor antagonist, together in an amount effective to treat said disease.

Accordingly, it is an object of the present invention to provide a novel method and composition for treating an airway disease. This and other objects are achieved in whole or in part by the present invention.

The foregoing and other objects and aspects of the present invention are explained in greater detail in the specification below.

DETAILED DESCRIPTION OF THE PREFERRED EMBODIMENTS

Examples of airway diseases that can be treated by the method of the present invention include cystic fibrosis, asthma, chronic obstructive pulmonary disease, bronchitis, and other airway diseases characterized by an inflammatory response. Treatment of airway inflammation is also provided in accordance with the present invention, including inflammation with or without (i.e. free of) asthma.

As used herein, the term "treat" or "treating" a lung disease refers to a treatment which decreases the likelihood that the subject administered such treatment will manifest symptoms of the lung disease. The term "downregulate" thus refers to inducing a decrease in production, secretion or availability (and thus a decrease in concentration) of the targeted intracellular protein.

"Concurrently administering" as used herein refers to the administration of two or more active agents sufficiently close in time to achieve a combined therapeutic effect that is preferably greater than that which would be achieved by the administration of either agent alone. Such concurrent administration can be carried out simultaneously, e.g., by administering the active agents together in a common pharmaceutically acceptable carrier.

The term "subject" as used herein refers to any vertebrate species. The methods of the present invention are particularly useful in the treatment of warm-blooded vertebrates. Thus, in a preferred embodiment, the invention concerns mammals and birds.

The present invention is concerned primarily with the treatment of human subjects but can also be employed for the treatment of other mammalian subjects, such as dogs, cat, livestock, primates and horses, for veterinary purposes.

Animals so treated can be warm-blooded vertebrates, for instance, mammals and birds. More particularly, the animal can be selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Most particularly, the animal can be a primate, such as an ape, a monkey, a lemur, a tarsier, a marmoset, or a human.

Thus, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

1. Adenosine $A_{2B}$ and Adenosine $A_3$ Receptor Antagonists.

Any compound that inhibits the activity of adenosine $A_{2B}$ and adenosine $A_3$ receptors are referred to as "active agents" herein (including their pharmaceutically acceptable salts). Such compounds are known, and include compounds that specifically (e.g., stereospecifically) bind to such adenosine receptors, as well as antisense oligonucleotides that downregulate the expression of such receptors. Antisense oligonucleotides are discussed in greater detail below. Compounds that specifically bind to adenosine $A_{2B}$ and $A_3$ receptors include, but are not limited to, those described in U.S. Pat. No. 6,117,878 and U.S. Pat. No. 6,048,865 (applicant specifically intends that the disclosures of all United States Patent references cited herein be incorporated herein by reference).

Examples of $A_{2B}$ adenosine receptor antagonists include, but are not limited to, enprofylline, alloxazine and MRS-1754.

Examples of $A_3$ adenosine receptor antagonists include, but are not limited to, MRS 12220, MRS-1191, MRS-1523, L-249313 and L-268605.

2. Antisense Oligonucleotides as Adenosine $A_{2B}$ and Adenosine $A_3$ Receptor Antagonists.

As used herein, "antisense oligonucleotide" has its typical meaning in the art, and can for example be a short sequence of synthetic nucleotides that (1) hybridizes to any coding sequence in an mRNA that codes for the targeted protein, and (2) upon hybridization causes a decrease in gene expression of the targeted protein. Antisense oligonucleotides can be of any suitable length e.g., from about 6, 8 or 10 to about 40, 60 or 100 nucleotides in length, depending on the particular target being bound and their mode of delivery.

The mRNA sequence and the sequence of the corresponding antisense oligonucleotide for the $A_{2B}$ or $A_3$ adenosine receptor is derived from the DNA base sequence of the gene expressing either the $A_{2B}$ or $A_3$ adenosine receptor. These genes are known (see, e.g., U.S. Pat. No. 5,441,883 to Civelli; U.S. Pat. No. 5,599,671 to Jacobson et al.; U.S. Pat. No. 5,854,081 to Linden et al.; U.S. Pat. No. 5,516,894 to Reppert). The antisense oligonucleotides that downregulate the production of the $A_{2B}$ or $A_3$ adenosine receptor can be produced in accordance with standard techniques (see e.g., U.S. Pat. Nos. 6,140,492; 6,117,848; 6,087,343; 6,018,042; 5,994,320).

The antisense oligonucleotides can be oligonucleotides in Which, for example, the phosphodiester bonds have been modified. Examples include, but are not limited to, compounds containing one or more linkages such as phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI) or methyleneoxy(methylimino) (MOMI) linkages. Where appropriate, the antisense oligonucleotides can be administered in the form of pharmaceutically acceptable salts.

In one embodiment the antisense oligonucleotide is directed to an mRNA region containing a junction between intron and exon. Where the antisense oligonucleotide is directed to an intron/exon junction, it can either entirely overlie the junction or can be sufficiently close to the junction to inhibit the splicing out of the intervening exon during processing of precursor mRNA to mature mRNA e.g., with the 3' or 5' terminus of the antisense oligonucleotide being positioned within about, for example, 10, 5, 3, or 2 nucleotides of the intron/exon junction.

3. Pharmaceutical Formulations and Administration.

Pharmaceutical compositions provided herein comprise the active agents (including their pharmaceutically acceptable salts) as given above. These compositions are administered in amounts effective to reduce the expression or antagonize the activity of the $A_{2B}$ and $A_3$ adenosine receptors. Such compositions are provided in a suitable pharmaceutically acceptable carrier e.g., sterile pyrogen-free saline solution. The active agent antisense oligonucleotides can additionally be formulated with a hydrophobic carrier capable of passing through a cell membrane, e.g., in a liposome, with the liposomes carried in a pharmaceutically acceptable aqueous carrier. The oligonucleotides can also be coupled to a substance that inactivates mRNA, such as a ribozyme.

Furthermore, the pharmaceutical formulation can also contain chimeric molecules comprising antisense oligonucleotide active agents attached to molecules that are known to be internalized by cells. These oligonucleotide conjugates utilize cellular uptake pathways to increase the cellular concentrations of oligonucleotides. Examples of macromolecules used in this manner include transferrin, asialoglycoprotein (bound to oligonucleotides via polylysine) and streptavidin.

In the pharmaceutical formulation the active agent can be contained within a lipid particle or vesicle, such as a liposome or microcrystal. The lipid particles can be of any suitable structure, such as unilamellar or plurilamellar, so long as the antisense oligonucleotide is contained therein. Positively charged lipids such as N-[1-(2, 3-dioleoyloxi) propyl]-N, N, N-trimethylammoniumethylsulfate, or "DOTAP," are particularly preferred for such particles and vesicles. The preparation of such lipid particles is well known. See e.g., U.S. Pat. No. 4,800,635 to Janoff et al.; U.S. Pat. No. 4,904,677 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The composition of the invention can be administered by any means that transports the active agents to the lung. The active agents disclosed herein can be administered to the lungs of a patient by any suitable means, but are preferably administered by generating an aerosol comprised of respirable particles, the respirable particles comprised of the active agents, which particles the subject inhales. The respirable particles can be liquid or solid, and they can optionally contain other therapeutic ingredients.

Figure 1:
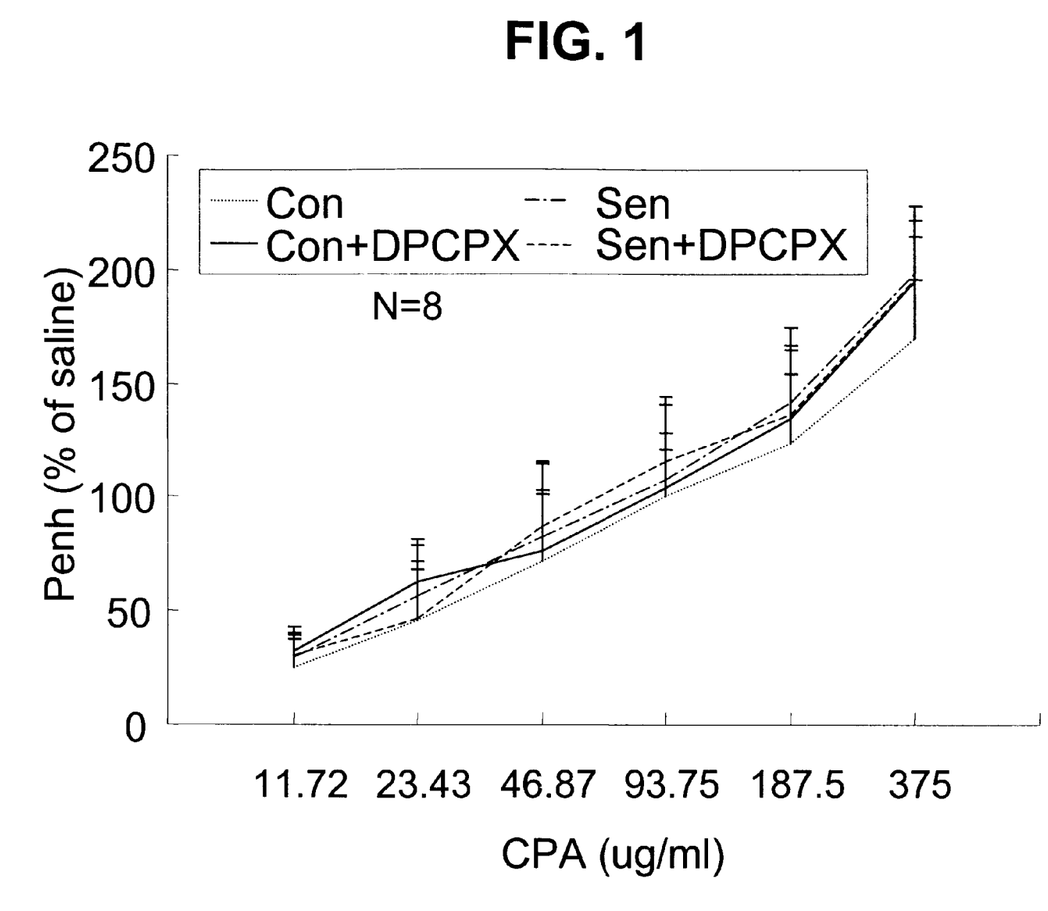
FIG. 1 illustrates the effect of DPCPX ($10^{-4}$ M) on dose-responsiveness to CPA (micrograms per milliliter—ug/ml) in a mouse model of asthma. Control (Con)=dotted line, sensitized (Sen)=broken line, Con+DPCPX=solid line, and Sen+DPCPX=dashed line. Penh=percentage of saline in all Figures.

Particles comprised of active agents for practicing the present invention should be administered as a formulation including particles of respirable size: that is, particles of a size sufficiently small to pass through the nose, mouth and larynx upon inhalation and into the bronchi and alveoli of the lungs. In general, respirable particles range from about 0.5 to 10 microns in diameter. Particles of non-respirable size that are included in the aerosol tend to deposit in the throat and be swallowed. Accordingly, the quantity of non-respirable particles in the aerosol is preferably minimized. For nasal administration, a particle size in the range of 10–500 $\mu$m is preferred to ensure retention in the nasal cavity. Alternatively, droplets can be given.

Liquid pharmaceutical compositions of active agents for producing an aerosol can be prepared by combining the active agents with a suitable vehicle, such as sterile pyrogen free water. Other therapeutic compounds can optionally be included.

Solid particulate compositions containing respirable dry particles of micronized active agents can be prepared by grinding dry antisense compound with a mortar and pestle, and then passing the micronized composition through a 400 mesh screen to break up or separate out large agglomerates. A solid particulate composition comprising the active agent can optionally contain a dispersant that serves to facilitate the formation of an aerosol. A suitable dispersant is lactose, which can be blended with the active agents in any suitable ratio e.g., a 1 to 1 ratio by weight.

The active agents can be administered in an amount which depends upon the disease being treated, the condition of the subject, the particular formulation, the route of administration, the timing of administration to a subject, etc. For administration to a subject such as a human, a dosage of from about 0.01, 0.1, or 1 mg/Kg up to 50, 100, or 150 mg/Kg or more for each active agents can be employed. Depending on the solubility of the particular formulation of active compounds administered, the daily dose can be divided among one or several unit dose administrations. The administration of the active compounds can be carried out therapeutically (i.e., as a rescue treatment) or prophylactically.

The aerosols of liquid particles comprising the active agents can be produced by any suitable means, such as with a nebulizer. See e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w, but preferably less than 20% w/w, of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

The aerosols of solid particles comprising the active agents can likewise be produced with any solid particulate medicament aerosol generator. Aerosol generators for administering solid particulate medicaments to a subject produce particles, which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders that can be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, surfactants, such as oleic acid or sorbitan trioleate, antioxidants and suitable flavoring agents.

The aerosol, whether formed from solid or liquid particles, can be produced by the aerosol generator at a rate of from about 10 to 150 liters per minute, more preferably from about 30 to 150 liters per minute, and most preferably about 60 liters per minute. Aerosols containing greater amounts of medicament can be administered more rapidly.

The present invention is explained in greater detail in the following non-limiting Examples.

EXAMPLE 1

FIG. 1 illustrates the effect of DPCPX ($10^{-4}$ M) on dose-responsiveness to CPA in a mouse model of asthma.

The animals were nebulized with DPCPX ($10^{-6}$ M) for 3 minutes and 15 minutes later the dose response to CPA was performed. n=8 for each group. CPA is an $A_1$ adenosine receptor agonist; DPCPX is an $A_1$ adenosine receptor antagonist. These data show no $A_1$ adenosine receptor involvement in a mouse model for asthma.

EXAMPLE 2

Figure 2:
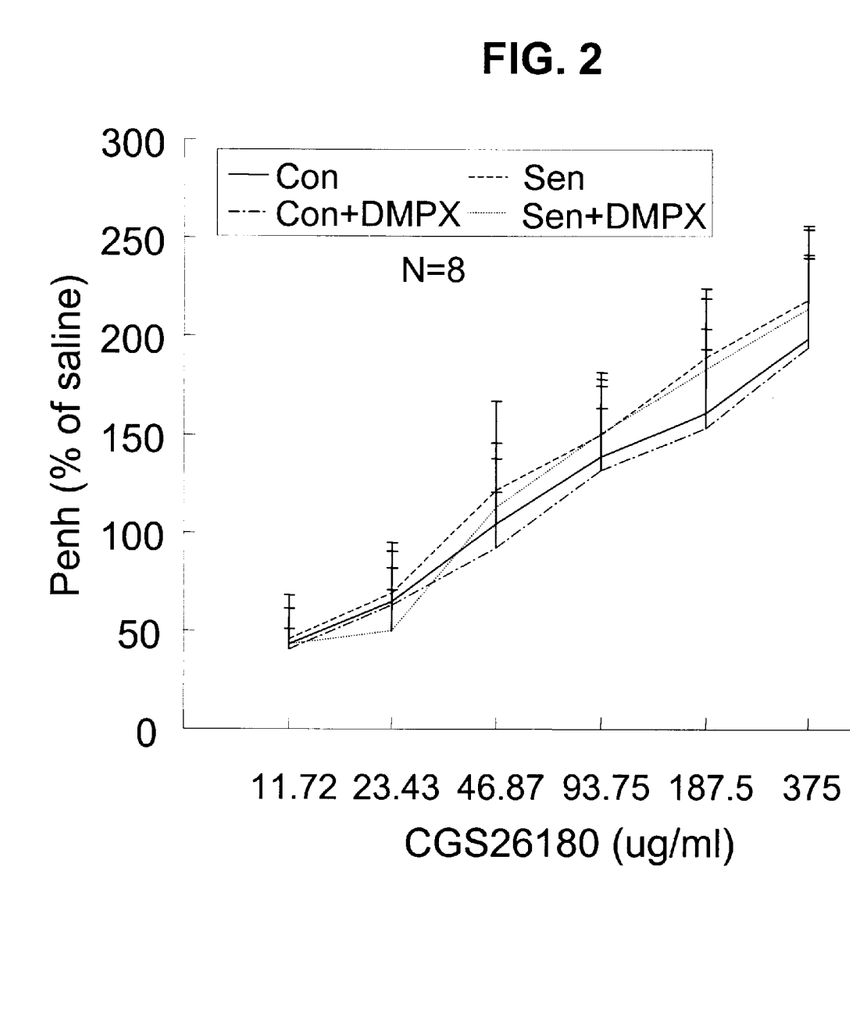
FIG. 2 illustrates the effect of DMPX ($10^{-4}$ M) on dose-responsiveness to CGS-26180 (ug/ml). Con=solid line, Sen=dashed line, Con+DMPX=broken line, and Sen+DMPX=dotted line.

FIG. 2 illustrates the effect of DMPX ($10^{-4}$ M) on dose-responsiveness to CGS-26180. The animals were nebulized with DMPX ($10^{-4}$ M) for 3 minutes and 15 minutes later the dose response to CGS-21680 was performed. n=8 for each group. CGS-21680 is an $A_{2A}$ adenosine receptor agonist; DMPX is an $A_{2A}$ adenosine receptor antagonist. These data show no $A_{2A}$ adenosine receptor involvement in a mouse model for asthma.

EXAMPLE 3

Figure 3:
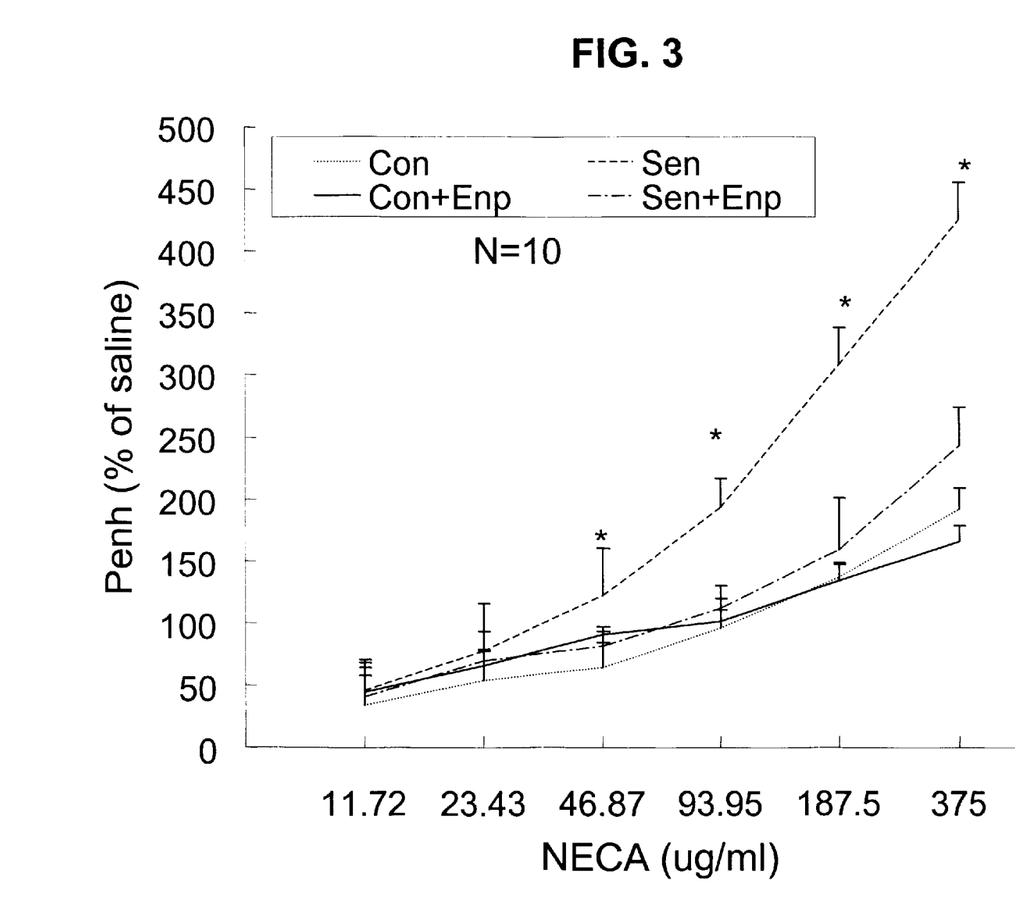
FIG. 3 illustrates the effect of enprofylline (enp; 12 mg/ml) on dose-responsiveness to 5'-(N-ethyl) carboxamidoadenosine (NECA, in ug/ml). Con=dotted line, Sen=dashed line, Con+enp=solid line, and Sen+enp=broken line.

FIG. 3 illustrates the effect of enprofylline (12 mg/ml) on dose-responsiveness to NECA. The animals were nebulized with enprofylline (12 mg/ml) for 1 minutes and 15 minutes later the dose-response to NMCA was performed. * p<0.05 compared to Sen+Enp group. # p<0.05 compared to control group. n=10 for each group. NECA is a non-selective adenosine receptor agonist; enprofylline is an $A_{2B}$ adenosine receptor antagonist. These data show the involvement of the $A_{2B}$ adenosine receptor in a mouse model of asthma. Note that enprofylline did not totally block the response.

EXAMPLE 4

Figure 4:
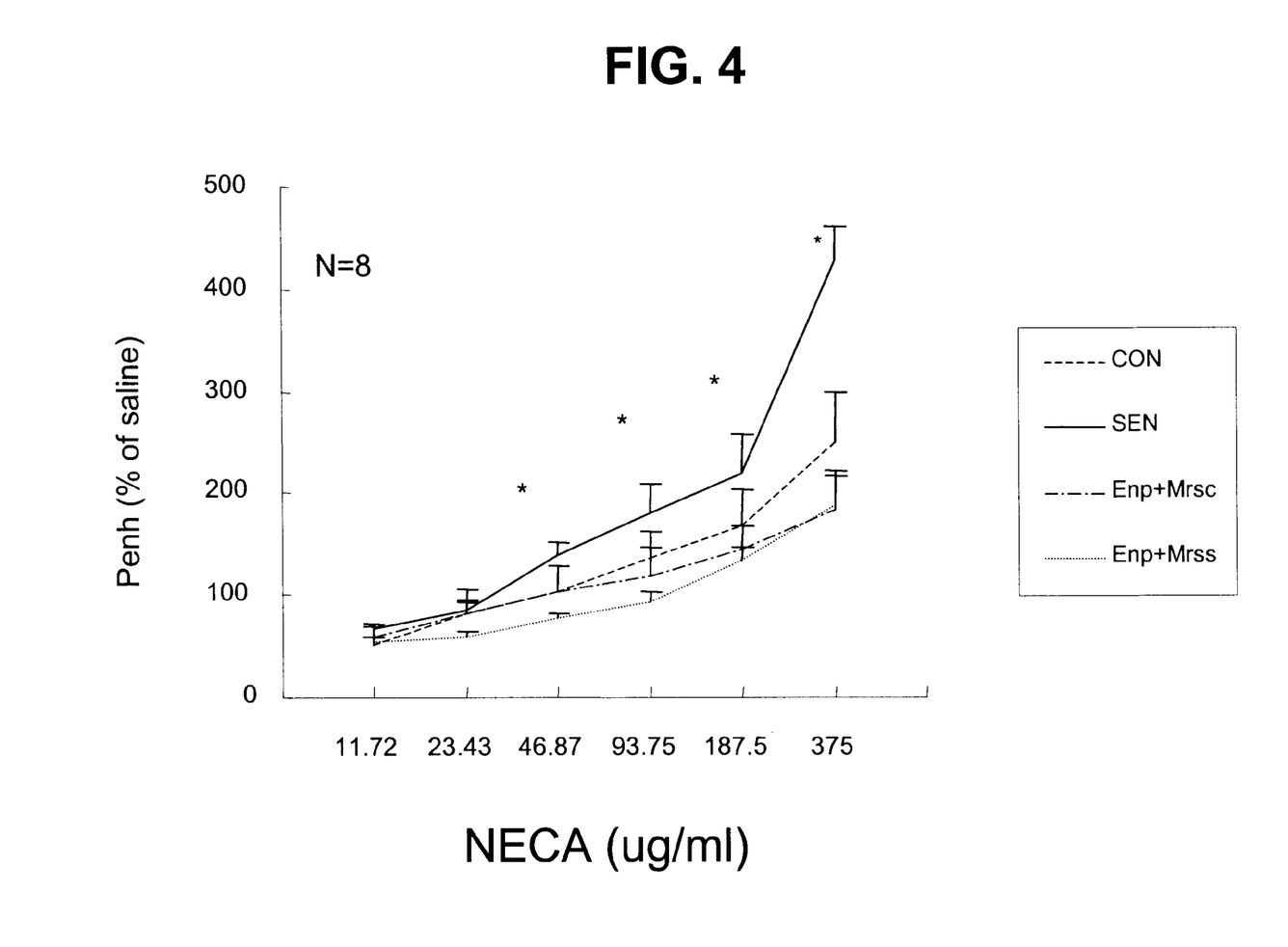
FIG. 4 shows the effect of enprofylline (12 mg/ml) and MRS1220 ($10^{-6}$ M) on dose response to NECA (ug/ml) in a mouse model of asthma. Control (CON)=dashed line, Sensitized (SEN)=solid line, Control Enp+MRS1220 (Enp+Mrsc)=broken line, and Sensitized Enp+MRS1220 (Enp+Mrss)=dotted line.

FIG. 4 shows the effect of enprofylline (12 mg/ml) and MRS1220 ($10^{-6}$ M) on dose response to NECA in a mouse model of asthma. MRS1220 is an $A_3$ adenosine receptor antagonist. These data show a substantially complete reversal of bronchospasm produced by NECA by the combination of $A_3$ (MRS1220) and $A_{2B}$ (enprofylline) antagonists in a mouse model of asthma.

EXAMPLE 5

Figure 5:
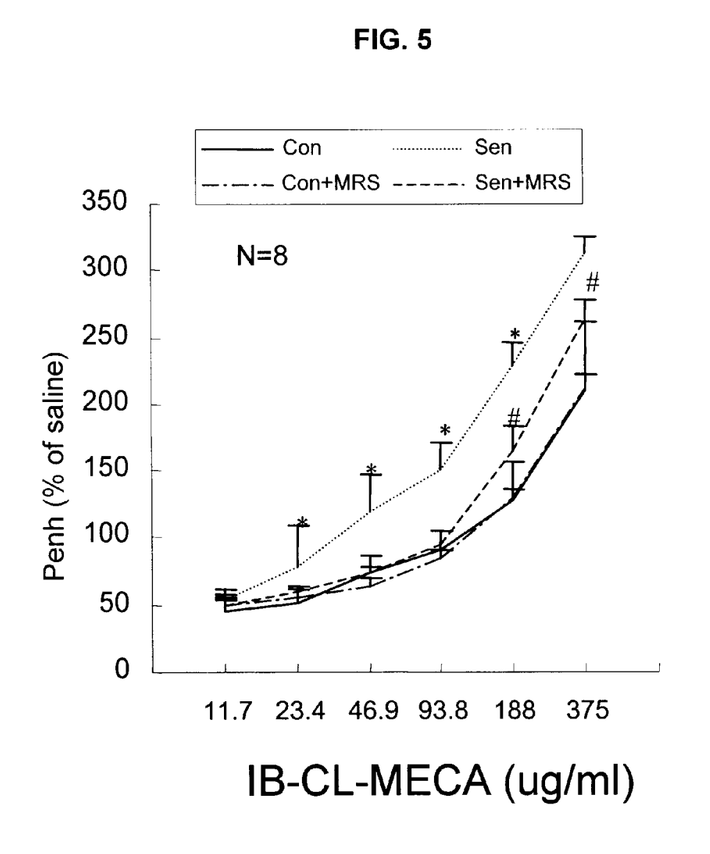
FIG. 5 shows the effect of MRS1220 ($10^{-6}$ M) on dose-responsiveness to IB-CL-5'-(N-methyl) carboxamidoadenosine (IB-CL-MECA, in ug/ml). Con=solid line, Sen=dotted line, Con+MRS=broken line, and Sen+MRS=dashed line.

FIG. 5 shows the effect of MRS1220 ($10^{-6}$ M) on dose-responsiveness to IB-CL-MECA. MRS1220 ($A_3$ antagonist) did not completely block the bronchospasm produced by C'-IB-CL-MECA. Therefore, the combination of $A_3$ and $A_{2B}$ antagonists appear better at blocking the adenosine-induced bronchospasm in a mouse model of asthma.

EXAMPLE 6

Figure 6:
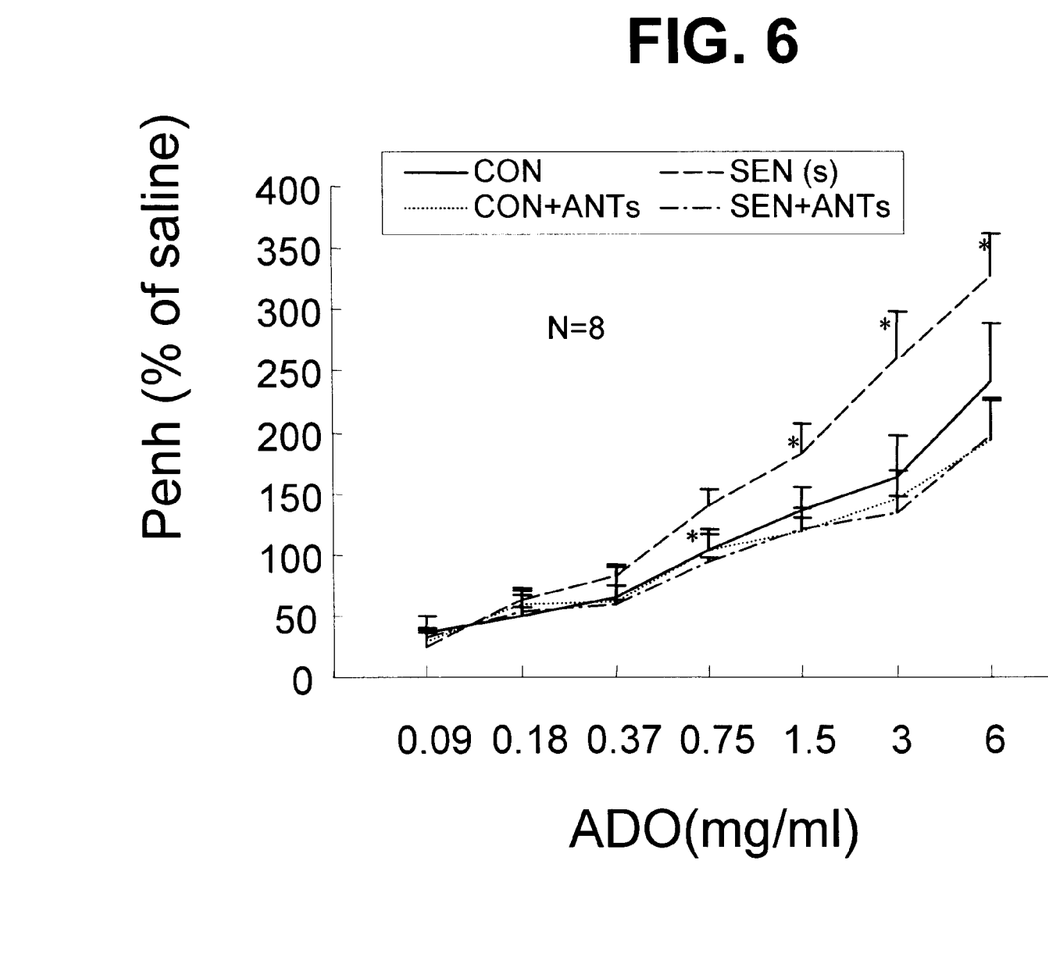
FIG. 6 shows the effects of the antagonists enprofylline and MRS1220 on dose-responsiveness to adenosine (ADO—milligrams per milliliter, mg/ml). Control (CON)=solid line, Sensitized (SEN)=dashed line, Control+Antagonists (CON+ANTs)=dotted line, and Sensitized+Antagonists (SEN+ANTs)=broken line.

FIG. 6 shows the effects of enprofylline (12 mg/ml) and MRS1220 ($10^{-4}$ M) on dose-responsiveness to adenosine. The animals were nebulized with enprofylline (12 mg/ml) and MRS1220 ($10^{-4}$ M) for 3 minutes and 15 minutes later the dose-response to adenosine was performed. ADO: adenosine. * p<0.05 compared to Enp+MRSs group. n=8 for each group. These data show the same conclusion as in connection with FIG. 4 above, with adenosine instead of NECA as a natural ligand.

EXAMPLE 7

Figure 7:
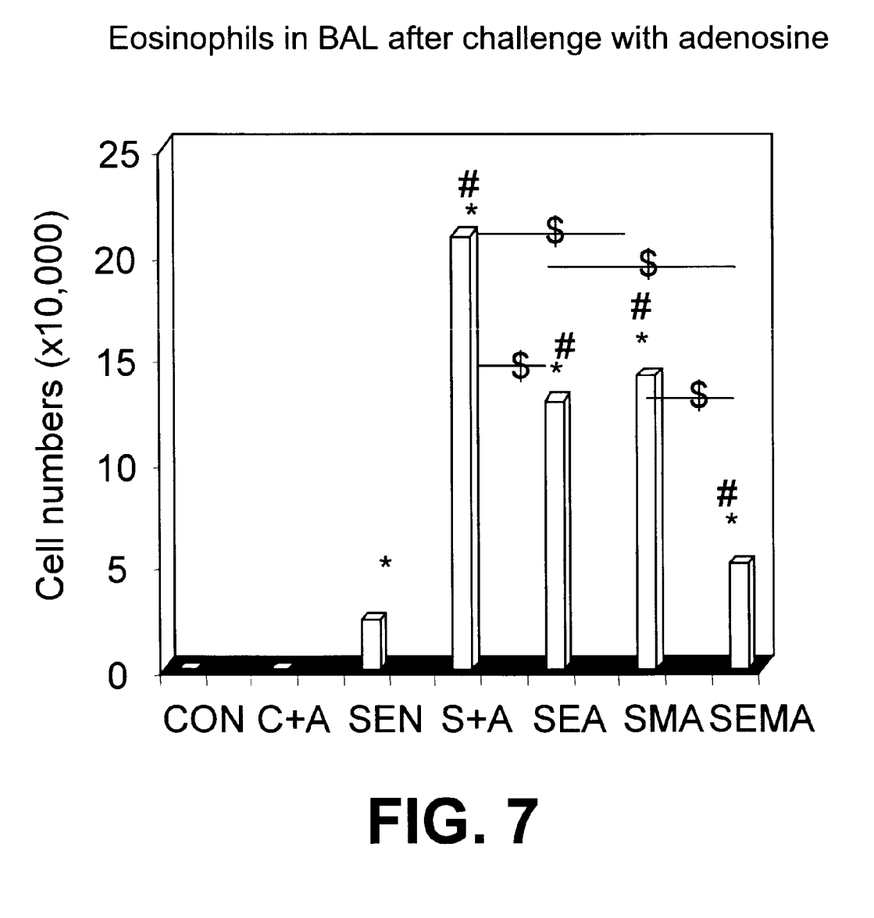
FIG. 7 shows the effects of enprofylline and MRS1220 on the recruitment of eosinophils in asthmatic lung. CON: control; C+A: control+adenosine (6 mg/ml, 2 min); SEN: sensitized; S+A: sensitized+adenosine; SEA: sensitized+enprofylline (12 mg/ml,3 min)+adenosine; SMA: sensitized+MRS1220 ($10^{-6}$ M, 3 min)+adenosine; SEMA: sensitized+enprofylline+MRS1220+adenosine. n=4 for each group. * $p<0.05$ compared to CON; # $p<0.05$ compared to SEN; $ $p<0.05$ between various groups indicated by horizontal line.

FIG. 7 shows the effects of enprofylline (12 mg/ml, 3 min) and MRS1220 ($10^{-6}$ M, 3 min) on the influx of eosinophils (inflammatory cell) into the lung (broncheo-alveolar lavage, BAL) in control and sensitized (asthma) groups after challenge with adenosine. The animals were nebulized with enprofylline and MRS1220 for 3 minutes and 15 minutes later challenged with an aerosol of adenosine at 6 mg/ml for 2 minutes. An hour later, the lungs were lavaged to collect the inflammatory cells. n=6 for each group. These data show that the combination of both $A_{2B}$ and $A_3$ adenosine receptors can greatly block the recruitment of eosinophils into the lung of asthmatic animals and thus, inflammation. This is characteristic of human asthma.

In FIG. 7, CON: control; C+A: control+adenosine (6 mg/ml, 2 min); SEN: sensitized; S+A: sensitized+adenosine; SEA; sensitized+enprofylline (12 mg/ml,3 min)+adenosine; SMA: sensitized+MRS1220 ($10^{-6}$ M, 3 min)+adenosine; SEMA: sensitized+enprofylline+MRS1220+adenosine. n=4 for each group. * p<0.05 compared to CON; # p<0.05 compared to SEN; $ p<0.05 between various groups indicated by horizontal line.

The foregoing is illustrative of the present invention, and is not to be construed as limiting thereof. The invention is defined by the following claims, with equivalents of the claims to be included therein.

That which is claimed is:

1. A method of treating an airway disease, airway inflammation, or both an airway disease and airway inflammation in a subject in need of such treatment, comprising concurrently administering to said subject an $A_3$ adenosine receptor antagonist and an $A_{2B}$ adenosine receptor antagonist, in an amount effective to treat said disease.

2. A method according to claim 1, wherein said airway disease is asthma and inflammation.

3. A method according to claim 1, wherein said $A_3$ adenosine receptor antagonist is an antisense oligonucleotide.

4. A method according to claim 1, wherein said $A_{2B}$ adenosine receptor antagonist is an antisense oligonucleotide.

5. A method according to claim 1, wherein said $A_{2B}$ adenosine receptor antagonist is enprofylline.

6. A method according to claim 1, wherein said $A_3$ adenosine receptor antagonist is MRS 1220.

* * * * *